United States Patent [19]

Tocker

[11] Patent Number: 4,632,694

[45] Date of Patent: Dec. 30, 1986

[54] ASYMMETRICAL TRIAZINE SALTS

[75] Inventor: Stanley Tocker, Wilmington, Del.

[73] Assignee: E. I. Du Pont de Nemours and Company, Wilmington, Del.

[21] Appl. No.: 740,031

[22] Filed: May 31, 1985

[51] Int. Cl.$^4$ .................. A01N 43/707; C07D 253/06
[52] U.S. Cl. ......................................... 71/93; 544/182
[58] Field of Search ............................. 71/93; 544/182

[56] References Cited

U.S. PATENT DOCUMENTS

| | | | |
|---|---|---|---|
| 3,671,523 | 6/1972 | Westphal et al. | 544/182 |
| 3,961,936 | 6/1976 | Westphal et al. | 71/93 |
| 4,057,417 | 11/1977 | Dickore et al. | 544/182 |

*Primary Examiner*—John M. Ford

[57] ABSTRACT

Asymmetrical triazine salts form stable formulations which are useful as agricultural chemicals.

16 Claims, No Drawings

ASYMMETRICAL TRIAZINE SALTS

BACKGROUND OF THE INVENTION

This invention relates to asymmetric triazine salts, which are useful as agricultural chemicals and, in particular, as herbicides, both general and selective.

In U.S. Pat. No. 4,036,632 compounds of the general formula are disclosed

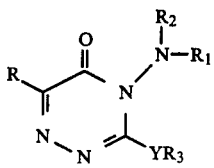

In the above formula R may be alkyl of $C_1$–$C_{18}$ carbon atoms, $R_1$ and $R_2$ may be hydrogen, Y may be O, S, or $NR_4$; wherein $R_4$ may be hydrogen or alkyl of $C_1$–$C_{18}$ carbon atoms and $R_3$ may be the same.

Although the compounds named in the '632 patent include outstanding herbicides, a need still exists for additional compounds which have even better properties such as handling characteristics. There is a need for compounds which form stable liquid formulations that are compatible with other herbicides. The need for such stability is readily apparent; often formulations of herbicides have to be stored in mixing tanks from which the material is applied to vegetation. If active ingredient crystallizes and settles out of the formulation, there will, of course, be that much less active ingredient for the purpose intended, i.e., herbicidal utility. Also the sedimentation can lead to clogged application equipment, especially spray nozzles. It is also often important to use combinations of herbicides since one herbicide normally will not destroy all of the undesired weed species. Thus, a herbicide which is readily compatible with other herbicides has a distinct advantage over herbicides that are incompatible with other herbicides.

SUMMARY OF THE INVENTION

This invention pertains to novel inorganic and organic acid salts of compounds of Formula I, compositions thereof and their use as preemergent and postemergent herbicides or as plant growth regulants.

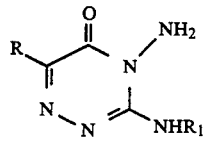

wherein
R is $C_1$–$C_8$ alkyl; and
$R_1$ is $C_1$–$C_3$ alkyl.

Preferred for reasons of their higher herbicidal activity, greater plant growth regulant activity, more favorable ease of synthesis and/or more favorable ease of use are:

(1) The hydrochloride salts of compounds of Formula I.
(2) Compounds of preferred 1 wherein R is $C_3$–$C_5$ branched alkyl; and
(3) Compounds of preferred 2 wherein R is tertiary butyl.

Specifically Preferred for their greatest herbicidal activity, greatest plant growth regulant activity, and/or greatest ease of synthesis:

4-amino-6-(1,1-dimethylethyl)-3-(methylamino)-1,2,4-triazin-5(4H)-one, hydrochloride salt; and
4-amino-6-(1,1-dimethylethyl)-3-(methylamino)-1,2,4-triazin-5(4H)-one, sulfate salt.

The compounds of this invention, and in particular, the specifically preferred compounds mentioned above, form stable aqueous solutions. This facilitates the preparation of extremely simple, low-cost agrichemical formulations, requiring no organic solvent or formulation adjuvants such as surfactants, dispersants or thickening agents. The resultant aqueous solutions are dilutable in all proportions with water.

Also, the aqueous salt solutions of the present invention show outstanding compatibility with aromatic hydrocarbon based herbicides, such as Treflan ® (trifluralin) or Tolban ® (profluralin) in terms of resistance to crystallization after dilution with water for agricultural application. Such compatibility helps insure accurate application rates and reduced plugging of application equipment such as spray nozzles.

DETAILED DESCRIPTION OF THE INVENTION

The compounds of Formula 1 can be used by the applicator as a solid particulate form or liquid aqueous concentrate. In either case, the material can be added to an appropriate amount of water, in which it readily dissolves, which would then be sprayed by the user to provide control of unwanted vegetation.

The salts of the present invention vary with respect to solubility in water, depending in part on the concentration of acid present. Stable concentrations containing up to 60% active material are possible, although 30–40% are more typical.

Although strong organic acids form salts of the compounds of Type 1, the preferred acids are hydrochloric and sulfuric. These acids react rapidly with the amino compounds of Type 1 to form salts containing relatively low-cost innocuous chloride or sulfate anions.

Although water is the preferred diluent for the salts of this invention, organic solvents such as alcohols and ketones can be used either as aqueous mixtures or alone.

The liquid solutions are desirable because of the ease with which they can be measured and poured or diluted in preparing sprayable concentrations of a given strength. Toxic dusts are thereby avoided, a problem commonplace with solid agrichemical formulations.

The herbicides of the present invention can be prepared according to the general process described in U.S. Pat. No. 4,036,632 which relates to the displacement of a 3-alkylthio group by an alkylamine. It is preferred that the 3-alkylthio compound be dispersed in water and heated with an excess of the appropriate $C_1$–$C_3$ primary amine. The preferred intermediates are methylamino, ethylamino, and isopropylamino compounds, formed by reaction of the 3-alkylthio intermediate with methylamine, ethylamine and isopopylamine, respectively. The resultant 3-alkylamino compound can be isolated by filtering off solid from the aqueous reactant mixture and drying. To form the salts of the present invention, slightly more than a molar excess of aqueous acid can be added to the 3-alkylamino triazines, using sufficient water to form a stable aqueous solution. In some cases the process can be simplified by reacting the aqueous alkylamino intermediate in the aqueous reaction dispersion with acid without isolation of the intermediate. When this process is used, the solid intermediate generally dissolves after a molar equivalent of acid is added.

Also, if desired the salts of the present invention can be readily isolated by stripping off solvent and volatile impurities in a rotary evaporator. The solid salt can be diluted to the desired concentration for packaging or application by dilution with the appropriate amount of water. Stable solutions containing up to 60% active ingredient can be readily prepared by dilution with water.

The preferred solvents for forming the salts are water or aqueous solutions containing an organic solvent such as a ketone or an alcohol. Other ingredients such as wetting agents or non-drift additives can be added to the salts or salt solutions if desired.

EXAMPLE 1

Preparation of
4-Amino-6-(1,1-dimethylethyl)-3-(methylamino)-1,2,4-triazine-5(4H)-one A mixture of 360 g of technical metrabuzin, 360 g water and 960 g of 40% aqueous methylamine was agitated in a sealed autoclave at 80° for 7.0 hours. The contents were cooled to room temperature and the solid was filtered off, dried in a circulating air oven at 50°, giving 225 g of crude product. Purification was achieved by recrystallization from 2.1 liters of ethanol to give 170 g of product. The structure was determined by NMR analysis, m.p. >230°.

EXAMPLE 2

Preparation of
4-Amino-6-(1,1-dimethylethyl)-3-(ethylamino)-1,2,4-triazine-5-(4H)-one A mixture of 150 g of technical metribuzin 200 g water and 100 g of 70% aqueous ethylamine was heated 90° for 7.0 hours in a stirred autoclave. The contents were cooled to room temperature, the solid filtered off and dried in a circulating air oven at 60°. The crude product was recrystallized from toluene to give 74 g of analytically pure product, m.p. 177°.

EXAMPLE 3

Preparation of
4-Amino-6-(1,1-dimethylethyl)-3-(isopropylamino)-1,2,4-triazine-5-(4H)-one A mixture of 20 g of technical metribuzin in 75 ml water and 28 ml isopropylamine was refluxed with stirring for 72 hours. The reactants were cooled and the solid product was isolated by filtration and drying. The m.p. was 158° and the structure was confirmed by elemental analysis and NMR analysis.

EXAMPLE 4

Hydrochloride Salt of the Product of Example 1

100 g of the product of Example 1 was stirred with 100 g of water followed by gradual addition of 55 g of concentrated hydrochloric acid. The water and excess hydrochloric acid were removed using a rotary evaporator and the residue was further dried in a vacuum oven at 75° to give 118 g of product. This salt melted at 207° and was characterized by elemental analysis and NMR analysis. It formed aqueous solutions, containing over 45% by weight of the salt, and showed no tendency to produce crystals after aging at 0° over 24 hours.

EXAMPLE 5

Hydrochloride Salt of the Product of Example 2

1.0 g of the product of Example 2 was treated successively with 1.0 g of water and 0.55 g of concentrated hydrochloric acid, giving a colorless solution that did not crystallize after aging at 0° for over 24 hours. The solution contained 45% by weight of the hydrochloride salt of Example 2. Water and excess acid were removed using a rotary evaporator and the product was dried in a vacuum oven at 75°, giving 1.17 g of the white salt, identified by elemental analysis and the NMR spectrum.

EXAMPLE 6

Sulfate Salt of the Product of Example 1

1.0 g of the product of Example 1 was treated successively with 2.0 g water and 0.62 g concentrated sulfuric acid, giving a colorless solution containing 34% of the sulfate salt of the product of Example 1. The product was not isolated. The resultant aqueous salt solution showed no crystallization after storage at 0° for over 24 hours.

EXAMPLE 7

Hydrochloride salt of the product of Example 3

1.0 g of the product of Example 3 was treated successively with 1.0 g of water and 0.61 g concentrated hydrochloric acid, to produce a 40% aqueous hydrochloride salt solution. The resultant solution showed no crystallization after storage at 0° for over 24 hours.

Utility

The compounds of the this invention have utility as herbicides and in particular as a selective herbicide for soybeans, corn and other crops. They have outstanding safety on some crops and also broad herbicidal activity; they may be applied preplant incorporated, pre-emergence or directed post-emergence.

The rates used may typically vary from about 50 to 350 g/ha depending on soil type, organic matter, weather, method of application and crop. One with ordinary skill in the art can select the proper rate to use in each instance. The compounds of the instant invention can be combined with other herbicides that are selective on soybeans, corn or other crops. A partial list of such compounds is given below.

| Common Name | Chemical Name |
|---|---|
| acifluorfen | 5-[2-chloro-4-(trifluoromethyl)-phenoxy]-2-nitrobenzoic acid |
| alachlor | 2-chloro-2'-6'-diethyl-N—(methoxymethyl)acetanilide |
| bifenox | methyl-5-(2,4-dichlorophenoxy)-2-nitrobenzoate |
| butachlor | N—(butoxymethyl)-2-chloro-2',6'-diethylacetanilide |
| CDAA | N—N—diallyl-2-chloroacetamide |
| chloramben | 3-amino-2,5-dichlorobenzoic acid |
| chloroxuron | 3-[p-(p-chlorophenoxy)phenyl]-1,1-dimethylurea |
| chloropropham | isopropyl m-chlorocarbanilate |
| diclofop | 2-[4-(2,4-dichlorophenoxy)-phenoxy]propanoic acid |
| dinoseb | 2-sec-butyl-4,6-dinitrophenol |
| diphenamid | N,N—dimethyl-2,2-diphenylacetamide |
| diquat | 6,7-dihydropyrido[1,2-a:2',1'-c]-pyrazinediium ion |

| Common Name | Chemical Name |
|---|---|
| glyphosate | N—(phosphonomethyl)glycine and agriculturally suitable salts thereof |
| isopropalin | 2,6-dinitro-N,N—dipropylcumidine |
| linuron | 3-(3,4-dichlorophenyl)-1-methoxy-1-methylurea |
| mefluidide | N—[2,4-dimethyl-5-[[(trifluoromethyl)sulfonyl]amino]phenyl]acetamide |
| metolachlor | 2-chloro-N—(2-ethyl-6-methylphenyl)-N—(2-methoxy-1-methylethyl)acetamide |
| monolinuron | 3-(p-chlorophenyl)-1-methoxy-1-methylurea |
| nitralin | 4-(methylsulfonyl)-2,6-dinitro-N,N—dipropylaniline |
| paraquat | 1,1'-dimethyl-4,4'-bipyridininium ion |
| pendimethalin | N—(1-ethylpropyl)-3,4-dimethyl-2,6-dinitrobenzeneamine |
| profluralin | N—(cyclopropylmethyl)-α,α,α-trifluoro-2,6-dinitro-N—propyl-p-toluidine |
| propachlor | 2-chloro-N—isopropylacetanilide |
| propham | isopropyl carbanilate |
| trifluralin | α,α,α-trifluoro-2,6-dinitro-N,N—dipropyl-p-toluidine |
| | 3-[[(4-methoxy-6-methyl-1,3,5-triazine-2-yl)aminocarbonyl]aminosulfonyl]9 thiophenecarboxylic acid, methyl ester |
| | 2-[[(4-chloro-6-methoxypyrimidin-2-yl)aminocarbonyl]aminosulfonyl]benzoic acid, ethyl ester |
| | 2-ethoxy-N—[[4-(2,2,2,-trifluoroethoxy)-6-methoxy-1,3,5-triazin-2-yl]aminocarbonyl]benzenesulfonamide |
| | N—[(4,6-dimethylpyrimidin-2-yl)aminocarbonyl]-2-(ethylsulfonyl)-5-methoxybenzenesulfonamide |
| | 2-(ethylsulfonyl)-5-methoxy-N—[(4-methoxy-6-methylpyrimidin-2-yl)aminocarbonyl]benzenesulfonamide |

The activity and selectivity of the compounds of this invention were discovered in the greenhouse tests shown below. In all the tests the active ingredient was 3-methylamino-4-amino-6-t-butyl-1,2,4-triazine-5-one hydrochloride. The test procedures and results follow.

Test A

Postemergence

Two round pans (25 cm diameter by 12.5 cm deep) were filled with Sassafras sandy loam soil. One pan was planted with blackgrass, sugar beets, nutsedge (*Cyperus rotundus*) tubers, rape (*Brassica napus*), crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xantium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed post-emergence with the active ingredient dissolved in an aqueous solution.

Preemergence

Two round pans (25 cm diameter by 12.5 cm deep) were filled with Sassafras sandy loam soil. One pan was planted with blackgrass, sugar beets, nutsedge, rape, crabgrass, sicklepod, teaweed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed pre-emergence with the active ingredient dissolved in an aqueous solution.

Treated plants and controls were maintained in the greenhouse for 28 days, then all treated plants were compared to controls and visually rated for plant response.

Response ratings are on a scale of 0 to 100 where 0=no effect, and 100=complete control. A dash (-) response means no test.

Response ratings are contained in Table 1.

TABLE 1

| Rate kg/ha | 4 | 16 | 62 | 250 |
|---|---|---|---|---|
| POST-EMERGENCE | | | | |
| Nutsedge | 0 | 0 | 0 | 0 |
| Crabgrass | 0 | 60 | 100 | 100 |
| Cassia | 0 | 40 | 100 | 100 |
| Teaweed | 0 | 40 | 100 | 100 |
| Rape | 0 | 20 | 100 | 100 |
| Jimsonweed | 20 | 90 | 100 | 100 |
| Velvetleaf | 0 | 50 | 100 | 100 |
| Blackgrass | 0 | 20 | 90 | 100 |
| Rice | 0 | 20 | 100 | 100 |
| Sugar beet | 30 | 100 | 100 | 100 |
| Wheat | 0 | 20 | 100 | 100 |
| Wild Oats | 0 | 0 | 0 | 0 |
| Cocklebur | 0 | 60 | 90 | 95 |
| Morningglory | 50 | 100 | 100 | 100 |
| Cotton | 20 | 90 | 100 | 100 |
| Johnsongrass | 0 | 30 | 60 | 100 |
| Barnyardgrass | 0 | 20 | 100 | 100 |
| Giant Foxtail | 0 | 20 | 100 | 100 |
| Soybean | 0 | 0 | 0 | 30 |
| Corn | 0 | 0 | 0 | 30 |
| PRE-EMERGENCE | | | | |
| Nutsedge | 0 | 0 | 0 | 0 |
| Crabgrass | 0 | 30 | 90 | 100 |
| Cassia | 0 | 20 | 80 | 100 |
| Teaweed | 0 | 30 | 80 | 100 |
| Rape | 0 | 0 | 50 | 100 |
| Jimsonweed | 0 | 30 | 90 | 100 |
| Velvetleaf | 0 | 30 | 100 | 100 |
| Blackgrass | 0 | 20 | 90 | 100 |
| Rice | 0 | 0 | 40 | 90 |
| Sugar beet | 0 | 20 | 100 | 100 |
| Wheat | 0 | 0 | 0 | 30 |
| Wild Oats | 0 | 0 | 0 | 60 |
| Cocklebur | 0 | 0 | 50 | 80 |
| Morningglory | 0 | 20 | 80 | 100 |
| Cotton | 0 | 0 | 70 | 100 |
| Johnsongrass | 0 | 0 | 70 | 70 |
| Barnyardgrass | 0 | 0 | 70 | 100 |
| Giant Foxtail | 0 | 30 | 90 | 100 |
| Soybean | 0 | 0 | 0 | 20 |
| Corn | 0 | 0 | 0 | 20 |

What is claimed is:

1. A storage stable herbicidal mixture consisting essentially of a herbicidal effective amount of an agriculturally suitable salt of a first compound selected from

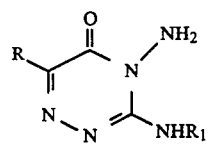

wherein
R is $C_1$-$C_8$ alkyl; and
$R_1$ is $C_1$-$C_3$ alkyl and a herbicidally effective amount of a second compound selected from N-(cyclopropylmethyl)-α,α,α-trifluoro-2,6-dinitro-N-propyl-p-toluidine or α,α,α-trifluoro-2,6-dinitro-N,N-dipropyl-p-toluidine in an aqueous solvent.

2. The mixture of claim 1 wherein the first compound is a hydrochloride salt.

3. The mixture of claim 1 wherein the first compound is a sulfate salt.

4. The mixture of claim 1 wherein R is $C_3$–$C_5$ branched alkyl.

5. The mixture of claim 4 wherein R is tertiary butyl.

6. The mixture of claim 1 wherein the first compound is 4-amino-6-(1,1-dimethylethyl)-3-(methylamino)-1,2,4-triazin-5(4H)-one, hydrochloride salt.

7. The mixture of claim 1 wherein the first compound is 4-amino-6-(1,1-dimethylethyl)-3-(methylamino)-1,2,4-triazin-5(4H)-one, sulfate salt.

8. The mixture of the compound of claim 6 and an effective amount of α,α,α-trifluoro-2,6-dinitro-N,N-dipropyl-p-toluidine.

9. A composition suitable for controlling the growth of undesired vegetation which comprises an effective amount of the mixture of claim 1 and at least one of the following: surfactant, solid or liquid diluent.

10. A composition suitable for controlling the growth of undesired vegetation which comprises an effective amount of the mixture of claim 2 and at least one of the following: surfactant, solid or liquid diluent.

11. A composition suitable for controlling the growth of undesired vegetation which comprises an effective amount of the mixture of claim 6 and at least one of the following: surfactant, solid or liquid diluent.

12. A composition suitable for controlling the growth of undesired vegetation which comprises an effective amount of the mixture of claim 8 and at least one of the following: surfactant, solid or liquid diluent.

13. A method for controlling the growth of undesired vegetation which comprises applying to the locus to be protected an effective amount of the mixture of claim 1.

14. A method for controlling the growth of undesired vegetation which comprises applying to the locus to be protected an effective amount of the mixture of claim 2.

15. A method for controlling the growth of undesired vegetation which comprises applying to the locus to be protected an effective amount of the mixture of claim 6.

16. A method for controlling the growth of undesired vegetation which comprises applying to the locus to be protected an effective amount of the mixtue of claim 8.

* * * * *